United States Patent [19]

Bridger et al.

[11] Patent Number: 5,817,807
[45] Date of Patent: Oct. 6, 1998

[54] ANTIVIRAL COMPOUNDS

[75] Inventors: Gary J. Bridger, Bryn Mawr; Sreenivasan Padmanabhan, Exton, both of Pa.; Renato T. Skerlj, Plainfield, N.J.; Pedro E. Hernandez-Abad, Malvern, Pa.; Milind P. Sant, Woburn, Mass.

[73] Assignee: Anormed Inc., Langley, Canada

[21] Appl. No.: 659,500

[22] Filed: Jun. 6, 1996

[30] Foreign Application Priority Data

Jun. 6, 1995 [GB] United Kingdom .................... 9511357

[51] Int. Cl.$^6$ .......................... A61K 31/44; A61K 31/33; C07D 257/00
[52] U.S. Cl. ........................... 540/474; 514/340; 514/183
[58] Field of Search ............................. 540/474; 514/340, 514/183

[56] References Cited

U.S. PATENT DOCUMENTS 5,021,409  6/1991  Murrer et al. .......................... 514/183

FOREIGN PATENT DOCUMENTS

WO 92/16494  10/1992  WIPO ........................... C07C 211/14
WO 93/12096   6/1993  WIPO ........................... C07D 257/02
WO 95/18808   7/1995  WIPO ........................... C07D 519/00

OTHER PUBLICATIONS

Martin et al. Helv. Chem. Chem. Soc., 73 (1990), 1, 149–153.
Morphy et al. J. Chem. Soc., Perkin Trans. 2 (1990), (4), 573–85.
Chemical Abstracts, 113:40649(1990).
Chemical Abstracts, 111:190197 (1987).
Chemical Abstracts, 123:56538 (1994).
Bridger et al, J. Med. Chem., 38:366–378 (1995).
De Clerco et al, Antimicrobial Agents and Chemotherapy, 38(4):668–74 (1994).

*Primary Examiner*—S. Mark Clardy
*Assistant Examiner*—Sabiha N. Qazi
*Attorney, Agent, or Firm*—Pillsbury Madison & Sutro LLP

[57] ABSTRACT

Macrocyclic compounds having 1, 4, 8, 11-tetraazacyclotetradecanyl group, show good selectivity against HIV-1 and HIV-2, in in vitro tests are disclosed.

5 Claims, No Drawings

ANTIVIRAL COMPOUNDS

The present invention concerns improved antiviral compounds. More especially, it concerns derivatives of monocyclic polyamines which have activity in standard tests against HIV-infected cells.

The disease known as Acquired Immune Deficiency Syndrome (AIDS) caused by infection with HIV has attracted immense research effort because of the effect of the disease on infected individuals, and the dangers of the disease spreading to a wider section of the population. In general, although various chemo-therapeutic treatments have been advocated, and some compounds have emerged as a potential basis for treatment, there is still a need for alternatives. In particular, most treatments such as AZT have a high toxicity to cells, and it would be desirable to find compounds which are less toxic. In man, the development of resistance to AZT has been identified as an additional clinical problem.

We have found a group of compounds which show protective properties in in vitro screens of cells challenged with HIV-1 and/or HIV-2, and are therefore indicated as having potential for the treatment of AIDS and AIDS-Related Complex, and other viral and especially retroviral infections. Accordingly the present invention provides the compounds of general formula I, defined below, having activity against HIV. A further aspect of the invention provides a process for the preparation of compounds of general formula I. The invention further provides the use of the compounds of formula I in the manufacture of a medicament for the treatment of HIV-infected patients. Pharmaceutical compositions according to the invention comprise the compounds of formula I in combination or association with a pharmaceutically acceptable diluent or excipient, for the treatment of HIV-infected patients. The invention yet further provides a method of treatment of a HIV-infected patient, comprising administering to said patient an effective dose of a said compound. It is to be understood that treatment includes prophylactic treatment of patients at risk, in view of the protective properties observed in tests. The use of the compounds may also be stated as including a method of treating HIV-infected or HIV-challenged human cells to prevent or modulate the multiplication of the HIV, comprising administering to said cells an effective dose of a said compound.

Our U.S. Pat. No. 5,021,409 describes linked cyclic polyamines as being active against HIV-1 and -2 in in vitro tests. Our WO93/12096 describes selected linked polyamine compounds as having very considerable Selectivity Indices (SI), eg greater than 5–10×10$^4$, in tests against HIV-1 and -2. We had also described, in WO92/16494, certain "long chain antiviral compounds", as having antiviral activity. Such long chain compounds had a polyheteroalkyl chain of 9 to 32 members, optionally linked through a linking atom or group, attached to a cyclic polyamine. The single compound tested showed a modest SI of 13.

Accordingly, the present invention provides a macrocyclic compound of general formula I

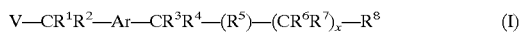  (I)

wherein V is a cyclic polyamine moiety having a total of 9 to 24 members and from 3 to 6 optionally substituted amine nitrogens spaced by two or more optionally substituted carbon atoms from each other, and which may optionally comprise a fused aromatic or heteroaromatic ring;
$R^1$ to $R^7$ may be the same or different and are independently selected from hydrogen or straight, branched or cyclic $C_{1-6}$ alkyl;

$R^8$ is a heterocyclic group, a substituted aromatic group, or a mercaptan group;
Ar is an aromatic or heteroaromatic ring each optionally substituted at single or multiple positions with electron-donating or withdrawing groups;
x is 1 or 2;
and the acid addition salts and metal complexes thereof.

Preferably V is a 14- to 17-membered fused or unfused ring system, such as a cyclam system or a 4,7,10,17-tetraazabicyclo[13.3.1]heptadeca-1(17),13,15-triene system or a derivative thereof, and especially a cyclam system or derivative thereof. The moiety V may be substituted at C or N non-linking atoms, suitably by hydroxyl, alkoxy, thiol, thioalkyl or any other atom or group which does not adversely affect the activity or toxicity of the compounds but may reduce the basicity of the amines, for example halogen, nitro, carboxy, carboxyamido, sulphonic acid or phosphate. Suitably the fused aromatic or heteroaromatic ring is phenyl, pyridine, pyrimidine, pyrazine, imidazole or thiazole. Preferably, the fused aromatic or heteroaromatic ring is phenyl or pyridine.

Preferably $R^1$ to $R^7$ are each hydrogen.

Preferably $R^8$ is selected from pyridine, pyrimidine, pyrazine, imidazole, thiophene, thiophenyl, aminobenzyl, piperidinyl, piperazinyl or a mercaptan group.

Preferably Ar is phenyl. Preferred substituents are alkyl, aryl, amino, alkoxy, hydroxy, halogen, carboxyl and carboxamido The invention also includes what may be termed as "pro-drugs", that is protected forms of the compounds, which release the compound after administration to a patient. For example, the compound may carry a protective group which is split off by hydrolysis in body fluids eg in the bloodstream, thus releasing active compound or are oxidised or reduced in body fluids to release the compound. A discussion of pro-drugs may be found in "Smith and Williams' Introduction to the Principles of Drug Design", H J Smith, Wright, Second Edition, London 1988.

Acid addition salts, for example hydrochlorides, and non-toxic labile metal complexes of compounds of formula I are also active compounds according to the present invention. Non-toxic in the present tense has to be considered with reference to the prognosis for the infected patient without treatment. Copper and zinc complexes are preferred although other metals such as nickel may be considered, whereas less labile metals such as cobalt and rhodium are less preferred because of likely lower selectivity.

Compounds of formula I are novel. Accordingly, a further aspect of the invention provides a process for the preparation of a compound of formula I which comprises the following steps:
(i) nucleophilic attack by the cyclic polyamine V having a single unprotected amine nitrogen, all other amine nitrogen atoms being protected, on an excess of a compound of formula II

  (II)

wherein $R^1$ to $R^4$ and Ar are as hereinbefore defined, and each Y is an active substituent which can be displaced by the unprotected nitrogen of polyamine V and is preferably selected from Br, Cl, I, methane sulphonate, 4-toluenesulphonate, trifluoromethane sulphonate.

It is well within the capabilities and knowledge of the skilled synthetic chemist to protect the amine nitrogens of cyclic polyamines, and it is preferred to use substitution by methanesulphonyl and/or toluenesulphonyl and/or diethoxyphosphonyl (see Bridger et al, J. Med. Chem. 1995, 38. 366–378; Bridger et al WO 93/12096).

The protected polyamine V is firstly reacted with a 5- to 10-fold excess of a compound of formula II in a solvent such as acetonitrite or dimethylformamide, tetrahydrofuran or dioxane and in the presence of a base, for example sodium carbonate or potassium carbonate. The reaction generally proceeds at room temperature to elevated temperature to give a cyclic polyamine in which all amine nitrogens are protected. In general, a mixture of products will be obtained and we have found that the product can conveniently be purified by silica gel chromatography or crystallisation.
(ii) Nucleophilic attack of a compound of formula III

wherein $R^5$ to $R^8$ and x are as hereinbefore defined on the product of the reaction described at (i) above, and subsequently de-protecting the amine nitrogens. The reaction with an excess of a compound of formula III is carried out under similar conditions to the reaction with the polyamine V.

The de-protection step is suitably carried out by re-fluxing the protected molecule in a mixture of aqueous HBr and acetic acid or concentrated sulphuric acid, or in the case of diethoxyphosphonyl in the presence of gaseous hydrogen chloride or gaseous hydrogen bromide in acetic acid.

As mentioned above, the compounds of the invention have activity against viral infections, especially retrovirus infections and specifically HIV. Accordingly a further aspect of the invention provides a compound of formula I for use in medicine. More specifically, there is provided the use of a compound of formula I in the manufacture of a medicament for the treatment of HIV-infected patients. In the alternative, there is provided a method of treating an HIV-infected patient comprising administering to said patient, a pharmaceutically effective amount of a compound of formula I. Although compounds of formula I could be administered as the raw material it is preferable to present them in the form of a pharmaceutical composition comprising a compound of formula I as active ingredient in admixture with a pharmaceutically acceptable diluent or carrier and optionally one or more other therapeutic ingredients, such compositions providing a further aspect of the invention.

In all aspects of the invention, it is understood that meso forms, enantiomers and resolved optically active forms of the compounds of formula I are also included. Also, it is to be considered within the invention, compounds of formula I diluted with non-toxic or other active substances.

The present invention will now be illustrated by the following preparative Examples.

GENERAL PROCEDURE A

1-[1-Methylene-4-(bromomethylene)phenylene]-4,8,11-tris(diethoxyphosphoryl)-1,4,8,11-tetraazacyclotetradecane.

To a stirred solution of 4,8,11-Tris(diethoxyphosphoryl)-1,4,8,11-tetraazacyclotetradecane (see Bridger et. al. J Med. Chem. 1995, 38, 366–378) (6.1 g, 0.01 mol) and $K_2CO_3$ (1.89 g, 0.013 mol) in $CH_3CN$ (150 ml) was added α,α'-dibromo-p-xylene (13.2 g, 0.05 mol) and the reaction mixture stirred at 70° C. for 1 hour. The solution was cooled to room temperature and the solvent removed under reduced pressure. The residue was partitioned between brine (50 ml) and $CH_2Cl_2$ (100 ml). The organic phase was separated, dried ($Na_2SO_4$) and concentrated to a minimum volume. The solid was filtered off and the solvent evaporated under reduced pressure to give the crude product as a pale yellow oil. Purification by column chromatography in silica gel ($CH_2Cl_2CH_3OH$, 25:1) gave 1-[1-methylene-4-(bromomethylene)phenylene]-4,8,11-tris(diethoxyphosphoryl-1,4,8,11-tetraazacyclotetra-decane (4.7 g, 59%) as a pale yellow oil. $^1H$ NMR ($CDCl_3$) δ 1.21–1.37 (m, 18 H), 1.66–1.74 (m, 2 H), 1.82–1.91 (m, 2 H), 2.30–2.35 (m, 2 H), 2.58–2.63 (m, 2 H), 2.99–3.16 (m, 12 H), 3.48 (s, 2 H), 3.95–4.07 (m, 12 H), 4.48 (s, 2 H), 7.21–7.35 (4 H).

GENERAL PROCEDURE B

Second alkylation of the bromobenzyl cyclam intermediate with an amine (see Scheme 2)

To a solution of the appropriate amine (5.0 equiv.) in dry $CH_3CN$ (5 mL) containing a suspension of $K_2CO_3$ (1.5 equiv.) at 80° C. was added dropwise with stirring a solution of 1-[1-methylene-4-(bromomethylene)phenylene]-4,8,11-tris(diethoxyphosphoryl-1,4,8,11-tetraazacyclotetradecane (0.6 mmol) in $CH_3CN$ (10 ml) over 15–20 min. After for a further 1 hour at 80° C. the solution was concentrated to dryness and the residue was partitioned between $CH_2Cl_2$ and water. The organic layer was separated and washed with water (3×) then dried ($MgSO_4$) and evaporated. The crude residue was purified by column chromatography on silica gel eluting with 5–15% MeOH/$CH_2Cl_2$ to afford a viscous oil.

GENERAL PROCEDURE C

De-protection of the diethoxyphosphoramidate groups using HBr/HOAc at room temperature (see Scheme 2, see also Bridger et al J. Med. Chem. 1995, 38, 366–378).

To a stirred solution of the protected cyclam derivative from procedure B (0.1–0.5 mmol) in acetic acid (3 mL) was added 30% HBr in acetic acid (Aldrich, 5 mL) and the solution was stirred at room temperature for 14 hours. The resulting precipitate was collected by filtration and washed with acetic acid then $Et_2O$. The solid was then dissolved in $H_2O$ (3 mL) and treated with charcoal (100 mg) and the mixture was heated to 80° C. for 30 min. The hot solution was filtered through celite and the filtrate was concentrated to approximately 1 mL after which acetic acid was added resulting in the immediate formation of a white precipitate. The white solid was collected by filtration and dried in vacuo.

The following compounds were prepared by these methods:

EXAMPLE 1

N-[1,4,8,11-Tetraazacyclotetradecanyl-1,4-phenylenebis(methylene)]-2-(aminomethyl)pyridine hexahydrobromide Mp 200°–205° C. (dec); $^1H$ NMR ($D_2O$) δ 2.04 (m, 4 H), 3.20–3.40 (m, 8 H), 3.40–3.60 (m, 8 H), 4.34 (s, 2 H), 4.38 (s, 2 H), 4.51 (s, 2 H), 7.50 (m, 4 H), 7.75 (t, 1 H, J=6.6 Hz), 7.82 (d, 1 H, J=7.9 Hz), 8.26 (t, 1 H, J=7.9 Hz), 8.63 (d, 1 H, J=5.3 Hz); $^{13}C$ NMR ($D_2O$) δ 18.30, 18.96, 37.04, 37.28, 37.40, 40.92, 41.13, 41.49, 44.26, 47.61, 48.01, 51.29, 58.88, 127.46, 127.75, 130.40, 131.05, 131.23, 131.47, 132.10, 132.44, 144.95, 145.81, 146.01; FAB MS m/z 493 M+H$^{81}$Br, 7), 491 (M+H$^{79}$Br, 7), 411 (M+H, 100);

Anal. ($C_{24}H_{38}N_6$·6HBr); Calc. C, 32.36; H, 4.98; N, 9.44; Br, 53.21. Found C, 32.20; H, 5.00; N, 9.30; Br, 53.10.

EXAMPLE 2

N-[1,4,8,11-Tetraazacyclotetradecanyl-1,4,phenylenebis(methylene)]-N-methyl-2-(aminomethyl)pyridine hexahydrobromide hydrate Mp 220°–225° C. (dec); $^1H$ NMR ($D_2O$) δ 2.06 (m, 4 H), 2.76 (s, 3 H), 3.20–3.65 (m, 16 H), 4.47 (bs, 4 H), 4.65 (s, 2 H), 7.54 (bs, 4 H), 7.80 (t, 1 H), 7.87 (d, 1 H), 8.28 (t, 1 H), 8.68 (d, 1 H); $^{13}$C NMR (D$_2$O) δ 18.14, 18.75, 18.89, 36.74, 37.04, 37.15, 37.62, 40.38, 40.72, 40.91, 41.28, 44.05, 47.50, 56.98, 58.88, 60.28, 127.60, 128.86, 130,78, 130.96, 132.16, 132.64, 144.91, 145.04, 146.12; FAB MS m/z 507 (M+H$_{40}$N$_6$.6HBr 1.5 H$_2$); Calc. C, 32.04; H, 5.27; n, 8.97; Br, 51.16. Found C, 31.88; H, 5.30; N, 8.93; Br, 51.00.

EXAMPLE 3

N-[1,4,8,11-Tetraazacyclotetradecanyl-1,4-phenylenebis(methylene)]-4-(aminomethyl)pyridine hexahydrobromide White solid: mp 201°–204° C. (dec); $^1$H NMR (D$_2$O) δ 1.91–2.12 (m, 4 H), 3.00–3.49 (m, 16 H), 4.13 (s, 2 H), 4.34 (s, 2 H), 4.53 (s, 2 H), 4.53 (s, 2 H), 7.39–7.57 (m, 4 H), 8.02 (d, 2 H, J=6.3 Hz), 8.74 (d, 2 H, J=6.3 Hz); $^{13}$C NMR (D$_2$O) δ 18.26, 18.88, 36.94, 37.29, 37.36, 40.89, 41.06, 41.44, 44.21, 47.61, 49.17, 51.43, 59.02, 127.84, 130.21, 131.64, 132.15, 132.45, 142.19, 151.67; FAB MS m/z 493 (M+H$^{81}$Br, 8), 491 (M+H$^{79}$Br, 10), 411 (M+H), 83), 320 (37), 247 (58), 201 (100). Anal. (C$_{24}$H$_{38}$N$_6$.6HBr). Calc. C, 32.17; H, 4.95; N, 9.34; Br, 53.50. Found C, 32.16; H, 5.03; N, 9.41; Br, 53.28.

EXAMPLE 4

N-[1,4,8,11-Tetraazacyclotetradecanyl-1,4-phenylenebis(methylene)]-3-(aminomethyl)pyridine hexahydrobromide White solid: mp 198°–202° C. (dec); $^1$H NMR (D$_2$O) δ 1.83–2.07 (m, 4 H), 2.96–3.47 (m, 16 H), 4.11 (s, 2 H), 4.32 (s, 2 H), 4.49 (s, 2 H), 7.38–7.56 (m, 4 H), 8.04 (t, 1 H, J=6.4 Hz), 8.63 (d, 1 H, J=8.3 Hz), 8.76 (d, 1 H, J=5.6 Hz), 8.86 (s, 1 H); $^{13}$C NMR (D$_2$O) δ 18.23, 18.87, 36.92, 37.29 (2 C), 40.88, 41.05, 41.43, 44.17, 47.22, 47.60, 51.18, 59.04, 128.29, 130.01, 131.49, 132.14, 132.66 (2 C), 142.55, 142.76, 148.98; FAB MS m/z 493 (M+H$^{81}$Br, 7), 491 (M+H$^{79}$Br, 6) 411 (M+H, 100), 320 (33), 247 (24). Anal. (C$_{24}$H$_{38}$N$_6$.6HBr). Calc. C, 32.17; H, 4.95; N, 9.34; Br, 53.50. Found C, 32.08; H, 5.02; N, 9.25; Br, 53.28.

EXAMPLE 5

N-[1,4,8,11-Tetraazacyclotetradecanyl-1,4-phenylenebis(methylene)]-(2-aminomethyl-5-methyl)pyrazine pentahydrobromide White solid: mp 194°–197° C. (dec); $^1$H NMR (D$_2$O) δ 1.93–2.12 (m, 4 H), 2.42 (s, 3 H), 3.25 (s, 8 H), 3.48 (s, 8 H), 4.28 (s, 2 H), 4.30 (s, 2 H), 4.33 (s, 2 H), 7.44 (s, 4 H), 8.33 (s, 1 H), 8.46 (s, 1 H); $^{13}$C NMR (D$_2$O) δ 18.01, 18.72, 19.80, 36.66, 37.05, 37.13, 40.70, 40.89, 41.27, 43.99, 47.47, 48.14, 50.61, 59.06, 129.97, 131.43, 132.04, 132.99, 140.93, 144.98, 146.49, 153.51; FAB MS m/z 509 (M+H$^{81}$Br, 17), 507 (M+H$^{79}$Br, 15), 426 (M+H, 100), 320 (21), 247 (20). Anal. (C$_{24}$H$_{39}$N$_7$.5.5 HBr). Calc. C, 33.10; H, 5.15; N, 11.26; Br, 50.47. Found C, 32.80; H, 5.41; N, 11.00; Br, 50.58.

EXAMPLE 6

N-[1,4,8,11-Tetraazacyclotetradecanyl-1,4-phenylenebis(methylene)]-2 -(aminoethyl)pyridine hexahydrobromide White solid: mp 195°–198° C. (dec); $^1$H NMR (D$_2$O) δ 1.98–2.17 (m, 4 H), 3.20–3.38 (m, 8 H), 3.38–3.63 (m, 12 H), 4.27 (s, 2 H), 4.39 (s, 2 H), 7.50 (s, 4 H), 7.80–7.89 (m, 2 H), 8.42 (m, 1 H), 8.58 (d, 1 H, J=5.8 Hz); $^{13}$C NMR (D$_2$O) δ 18.51, 19.14, 29.85, 37.56 (3 C), 41.21, 41.41, 41.82, 44.57, 45.27, 47.83, 51.10, 58.74, 126.35, 127.93, 130.66, 131.27, 131.99, 132.69, 141.89, 147.79, 150.91; FAB MS m/z 507 (M+H$^{81}$Br, 40), 505 (M+H$^{79}$Br, 34), 425 (M+H, 100).
Anal. (C$_{25}$H$_{40}$N$_6$.6HBr). Calc. C, 32.99; H, 5.09; N, 9.23; Br, 52.67. Found C, 32.79; H, 5.34; N, 9.11; Br, 52.45.

EXAMPLE 7

N-[1,4,8,11-Tetraazacyclotetradecanyl-1,4-phenylenebis(methylene)]-2-(aminomethyl) thiophene pentahydrobromide White solid: mp 245°–248° C. (dec); $^1$H NMR (D$_2$O) δ 1.87–2.12 (m, 4 H), 3.02–3.51 (m, 16 H), 4.17 (s, 4 H), 4.38 (s, 2 H), 6.97 (t, 1 H, J=3.9 Hz), 7.13 (d, 1 H, J=3.1 Hz), 7.41 (s, 5 H); 13C NMR (D$_2$O) δ 18.80, 19.52, 38.03, (3 C), 41.59 (2 C), 42.21, 44.89 (2 C), 48.15, 49.83, 58.52, 128.13, 129.12, 131.15, 131.47, 131.50, 131.90, 132.42, 132.87; FAB MS m/z 498 (M+H$^{81}$Br, 11), 496 (M+H$^{79}$Br, 9), 416 (M+H, 53), 218 (100), 201 (64).
Anal. (C$_{23}$H$_{37}$N$_5$S.5HBr). Calc. C, 33.68; H, 5.16; N, 8.54; Br, 48.71. Found C, 33.85; H, 5.22; N, 8.50; Br, 48.52.

EXAMPLE 8

N-[1,4,8,11-Tetraazacyclotetradecanyl-1,4-phenylenebis(methylene)]-2-(aminoethyl)mercaptan pentahydrobromide dihydrate White solid: mp 234°–236° C. (dec); $^1$H NMR (D$_2$O) δ 1.75–2.05 (m, 4 H), 2.75–3.45 (m, 20 H), 4.05 (s, 2 H), 4.15 (s, 2 H), 7.35 (s, 4 H). FAB MS m/z 462 (MH+H$^{81}$Br, 15), 460 (MH+H$^{79}$Br, 15), 380 (M+H, 100), 300 (64), 279 (47), 239 (49).
Anal. (C$_{20}$H$_{37}$N$_5$S.5HBr.2H$_2$O.0.5HOAc) requires C, 29.67; H, 5.69; N, 8.24; Br, 46.99. Found C, 29.31; H, 5.72; N, 8.25; Br, 46.64.

EXAMPLE 9

N-[1,4,8,11-Tetraazacyclotetradecanyl-1,4-phenylenebis(methylene)]-2-aminobenzylamine pentahydrobromide.

White solid: mp 203°–206° C. (dec.); $^1$H NMR (D$_2$O) δ 1.85–2.13 (m, 4 H), 3.02–3.58 (m, 16 H), 4.23 (s, 2 H), 4.31 (s, 4 H), 7.23–7.54 (m, 8 H); $^{13}$C NMR (D$_2$O) δ 18.03, 19.29, 37.78, (3 C), 41.37 (2 C), 42.00, 44.82, 46.25, 47.96, 51.16, 58.68, 124.04, 124.40, 129.40, 130.75, 131.21 (2 C), 131.88, 131.96, 132.46, 132.83; FAB MS m/z 507 (M+H$^{81}$Br, 15), 505 (M+H$^{79}$Br, 18), 425 (M+H, 100), 320 (30), 201 (51).
Anal. (C$_{25}$H$_{40}$N$_6$.5.75HBR.0.5H$_2$). Calc. C, 33.42; H, 5.19; N, 9.35; Br, 51.14. Found C, 33.69; H, 5.35; N, 9.00; Br, 51.13.

EXAMPLE 10

N-[1,4,8,11-Tetraazacyclotetradecanyl-1,4-phenylenebis(methylene)]-4-aminobenzylamine hexahydrobromide.

Yellow solid, mp=120°–125° C.; $^1$H NMR (D$_2$O) δ 1.8–2.0 (m, 4 H), 2.9–3.4 (m, 16 H), 4.1 (s, 2 H), 4.18 (s, 4 H), 7.2–7.5 (m, 8 H); $^{13}$C NMR (D$_2$O) δ 18.86, 19.57, 38.14, 41.76, 43.74, 45.14, 48.24, 50.14, 50.42, 51.49, 58.38, 124.13, 131.13, 131.30, 131.83, 131.92, 131.96, 132.67; FAB MS m/z 507 (MH+H$^{81}$Br, 5), 505 (MH+H$^{79}$Br, 5), 425 (M+H, 45), 201 (47), 155 (75), 106 (100).

Anal. ($C_{25}H_{40}N_6$.6HBr.HOAc) requires C, 33.43; H, 5.19; N, 8.66; Br, 49.42; O, 3.30. Found C, 33.42; H, 5.49; N, 8.62; Br, 49.23.

EXAMPLE 11

N-[1,4,8,11-Tetraazacyclotetradecanyl-1,4-phenylenebis(methylene)]-4-(aminoethyl)imidazole hexahydrobromide.

Off white solid, mp=135°–140° C. (dec.); $^1$H NMR ($D_2O$) δ 1.75 (m, 2 H), 1.90 (m, 2 H), 2.70–3.27 (m, 20 H), 3.77 (s, 2 H), 4.14 (s, 2 H), 7.18 (s, 1 H), 7.25 (d, 2 H, J=7.97 Hz), 7.37 (d, 2 H, J=7.97 Hz), 8.48 (s, 1 H); FAB MS m/z 496 (MH+$^{81}$Br, 5), 494 (MH+H$^{79}$Br, 5), 414 (M+H, 17), 201 (15).

Anal. ($C_{23}H_{39}N_7$.6HBr) requires C, 30.73; H, 5.04; N, 10.91; Br, 53.32. Found C, 30.39; H, 5.41; N, 10.41; Br, 53.66.

EXAMPLE 12

N-[1,4,8,11-Tetraazacyclotetradecanyl-1,4phenylenebis(methylene)]-benzylamine pentahydrobromide Off white solid, mp=245°–250° C. (dec.); $^1$H NMR ($D_2O$) δ 1.9–2.1 (m, 4 H), 3.2–3.6 (m, 16 H), 4.12 (s, 2 H), 4.15 (s, 2 H), 4.36 (s, 2 H), 7.30 (s, 5 H), 7.41 (d, 2H, J=8.3 Hz), 7.46 (d, 2 H, J=8.3 Hz); $^{13}$C NMR ($D_2O$) δ 18.43, 19.06, 37.29, 37.46, 37.63, 41.09, 41.32, 41.68, 44.46, 47.74, 50.18, 51.00, 58.79, 129.53, 129.97, 130.18, 130.35, 130.68, 131.18, 131.92, 133.14. FAB MS m/z 492 (MH+H$^{81}$Br, 13), 490 (MH+H$^{79}$Br, 13), 410 (M+H, 100), 201 (36). Anal. ($C_{25}H_{39}N_5$.5HBr) requires C, 36.88; H, 5.45; N, 8.60; Br, 49.07. Found C, 36.79; H, 5.56; N, 8.48; Br, 48.79.

The compounds of the invention were tested in a screen by the MTT method (J. Virol. Methods 120:309–321[1988]. MT-4 cells (2.5×10$^4$/well) were challenged with HIV-1 (HTLV-IIIB) or HIV-2 (LAV-2 ROD) at a concentration of 100 CCID$_{50}$ and incubated in the presence of various concentrations of the test compounds, which were added immediately after challenge with the virus. After 5 days culture at 37° C. in a $CO_2$ incubator, the number of viable cells was assessed by the MTT (tetrazolium) method. Antiviral activity and cytotoxicity of the compounds are expressed in the Table below as EC$_{50}$ (μg/ml) and CC$_{50}$ (μg/ml), respectively. The potential therapeutic usefulness was assessed by calculating a Selectivity Index (SI) corresponding to the ratio of CC$_{50}$ to EC$_{50}$.

TABLE 1

Anti-HIV activity data

| Compound | CC$_{50}$ (μg/mL) | EC$_{50}$ (μg/mL) HIV-1 (IIIB) | HIV-2 | SI HIV-1 |
|---|---|---|---|---|
| 1 | >250 | 0.008 | 0.032 | 3 × 10$^4$ |
| 2 | >250 | 0.1 | 6.7 | 2.5 × 10$^4$ |
| 3 | >250 | 0.6 | 10.3 | 417 |
| 4 | >250 | 1.8 | 28.5 | 138 |
| 5 | >250 | 0.2 | 7.1 | 1.2 × 10$^4$ |
| 6 | >250 | 1.8 | 3.8 | 138 |
| 7 | 158 | 0.7 | 9.8 | 225 |
| 8 | 175 | 0.5 | 2.0 | 350 |
| 9 | 153 | 0.8 | 10.6 | 191 |

TABLE 1-continued

Anti-HIV activity data

| Compound | CC$_{50}$ (μg/mL) | EC$_{50}$ (μg/mL) HIV-1 (IIIB) | HIV-2 | SI HIV-1 |
|---|---|---|---|---|
| 10 | 222 | 0.7 | 3.7 | 3 × 10$^3$ |
| 11 | 239 | 0.2 | 1.0 | 1 × 10$^4$ |
| 12 | 130 | 0.4 | 2.6 | 325 |

In this field of study, it is considered that any compound exhibiting a Selectivity Index of greater than 100 has the considerable potential for further study. HIV is one of the most challenging viruses to combat, and the results given above provide an indication of activity against other retroviruses and against other viruses in general.

The active compounds may be administered in the form of pharmaceutical composition formulated according to well known principles and incorporating the compound, preferably in unit dose form, in combination with a pharmaceutically acceptable diluent or excipient. Such compositions may be in the form of solutions or suspensions for injection, or irrigation or be in capsule, tablet, dragee, or other solid composition or as a solution or suspension for oral administration or formulated into pessaries or suppositories or sustained release forms of any of the above for implantation. Suitable diluents, carriers, excipients and other components are well known. It may be desirable also to formulate a composition for topical administration such as an ointment or cream. The compounds of the invention may be used, in the form of a composition or alone.

The pharmaceutical compositions according to the invention may be formulated in unit dosages determined in accordance with conventional pharmacological methods, suitably to provide active compounds in the dosage range in humans of from 0.1 to 100 mg/kg body weight per day, in a single dose or in a number of smaller doses. Preferred dosage ranges are 1 to 30 mg/kg body weight per day iv or ip. Other active compounds may be used in the compositions or such active compounds or supplemental therapy may be included in a course of treatment.

We claim:

1. A macrocyclic compound of general formula I,

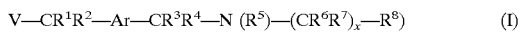

$$V—CR^1R^2—Ar—CR^3R^4—N\,(R^5)—(CR^6R^7)_x—R^8 \qquad (I)$$

wherein V is a 1,4,8,11-tetraazacyclotetra- decanyl group;
  $R^1$ to $R^7$ may be the same or different and are independently selected from hydrogen or straight, branched or cyclic $C_{1-6}$alkyl;
  $R^8$ is a pyridine, pyrimidine, pyrazine, imidazole, thiophene, thiophenyl, aminobenzyl, piperidinyl, piperazinyl group, or a mercaptan group;
  Ar is a phenylene ring optionally substituted with an electron donating or withdrawing group selected from the group consisting of alkyl, aryl, amino, alkoxy, hydroxy, halogen, carboxyl and carboxamido;
  x is 1 or 2;
  and the acid addition salts and metal complexes thereof.

2. A method of treating an HIV-infected patient comprising administering to said patient a pharmaceutically effective amount of a compound according to claim 1.

3. A pharmaceutical composition comprising as active ingredient a compound according to claim 1, in admixture with a pharmaceutically acceptable diluent or carrier and optionally one or more other therapeutic ingredients.

4. A composition according to claim 3, in unit dosage form.

5. A compound of claim 1 which is
N-[1,4,8,11-tetraazacyclotetra-decanyl-1,4phenylenebis-(methylene)]-2-(aminomethyl)pyridine;
N-[1,4,8,11-tetraazacyclotetra-decanyl-1,4-phenylenebis(methylene)]-N-methyl-2-(aminomethyl)pyridine;
N-[1,4,8,11-tetraazacyclotetra-decanyl-1,4phenylenebis(methylene)]-4-(aminomethyl)pyridine;
N-[1,4,8,11-tetraazacyclotetra-decanyl-1,4-phenylenebis(methylene)]-3-(aminomethyl)pyridine;
N-[1,4,8,11-tetraazacyclotetra-decanyl-1,4-phenylenebis(methylene)]-(2-aminomethyl-5-methyl)pyrazine;
N-[1,4,8,11-tetraazacyclotetra-decanyl-1,4-phenylenebis(methylene)]-2-(aminoethyl) pyridine;
N-[1,4,8,11-tetraazacyclotetra-decanyl-1,4-phenylenebis(methylene)]-2-(aminomethyl)thiophene;
N-[1,4,8,11-tetraazacyclotetra-decanyl-1,4-phenylenebis(methylene)]-2-(aminomethyl)mercaptan;
N-[1,4,8,11-tetraazacyclotetra-decanyl-1,4-phenylenebis(methylene)]-2-aminobenzylamine;
N-[1,4,8,11-tetraazacyclotetra-decanyl-1,4-phenylenebis(methylene)]-4-aminobenzylamine;
N-[1,4,8,11-tetraazacyclotetra-decanyl-1,4-phenylenebis(methylene)]-4-(aminoethyl)imidazole; or
N-[1,4,8,11-tetraazacyclotetra-decanyl-1,4-phenylenebis(methylene)]-benzylamine.

* * * * *